(12) United States Patent
Davidson et al.

(10) Patent No.: US 6,527,710 B1
(45) Date of Patent: Mar. 4, 2003

(54) SPECULUM

(75) Inventors: Gale E. Davidson, Indianapolis, IN (US); Kathryn L. Hier, Indianapolis, IN (US)

(73) Assignee: Hier Spec, Inc., Indianapolis, IN (US)

( * ) Notice: Subject to any disclaimer, the term of this patent is extended or adjusted under 35 U.S.C. 154(b) by 0 days.

(21) Appl. No.: 09/720,499

(22) PCT Filed: Jun. 30, 1999

(86) PCT No.: PCT/US99/14838

§ 371 (c)(1),
(2), (4) Date: Dec. 27, 2000

(87) PCT Pub. No.: WO00/02487

PCT Pub. Date: Jan. 20, 2000

Related U.S. Application Data

(60) Provisional application No. 60/092,301, filed on Jul. 10, 1998.

(51) Int. Cl.$^7$ ................................. A61B 1/32
(52) U.S. Cl. ......................... 600/222; 600/219
(58) Field of Search ................. 600/201, 210, 600/211, 216, 219, 220, 235, 222

(56) References Cited

U.S. PATENT DOCUMENTS 196,600 A * 10/1877 Shiland ...................... 600/201
325,647 A * 9/1885 Bailey ......................... 600/222

FOREIGN PATENT DOCUMENTS

DK          59995 A  *  7/1942

* cited by examiner

Primary Examiner—Jeffrey A. Smith
(74) Attorney, Agent, or Firm—Woodard, Emhardt, Naughton, Moriarty & McNett

(57) ABSTRACT

A speculum (18) including a combined first speculum blade and handle portion (20), a combined second speculum blade and link portion (62), a speculum handle portion and a plurality of combined ribs and links (76). Each of the combined ribs and links (76) is movably coupled to the combined first speculum blade and handle portion (20) and to the combined second speculum blade and link portion (62) to movably couple the combined first speculum blade and handle portion (20) to the combined second speculum blade and link portion (62). The speculum handle portion (46) is movably coupled to the combined first speculum blade and handle portion (20) and to the combined second speculum blade and link portion (62) to actuate the combined first speculum blade and handle portion (20) and the combined second speculum blade and link portion (62) relative to each other between a first orientation (illustrated in FIG. 4) in which the speculum (18) is configured to be inserted into an incision, meatus or the like, and a second orientation (illustrated in FIG. 5) in which the speculum is configured to aid in examination, treatment or the like, of the incision, meatus or the like.

16 Claims, 2 Drawing Sheets

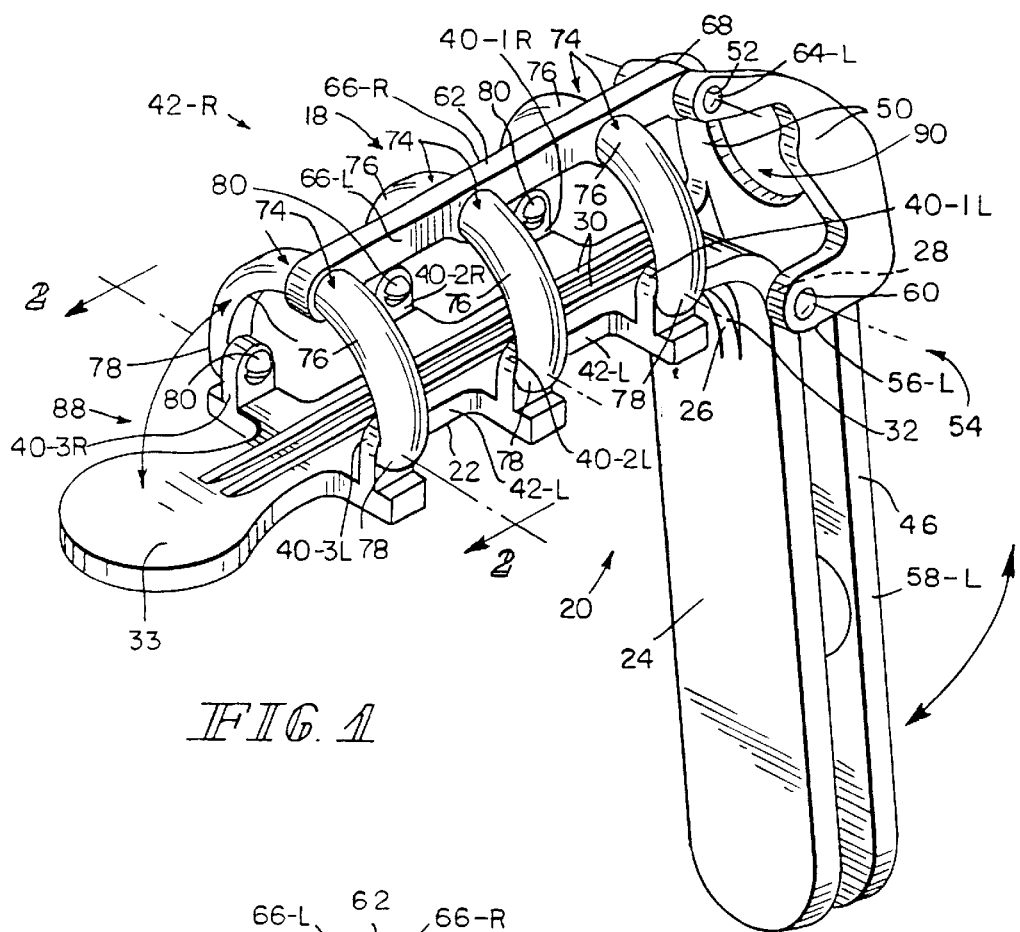
FIG. 1
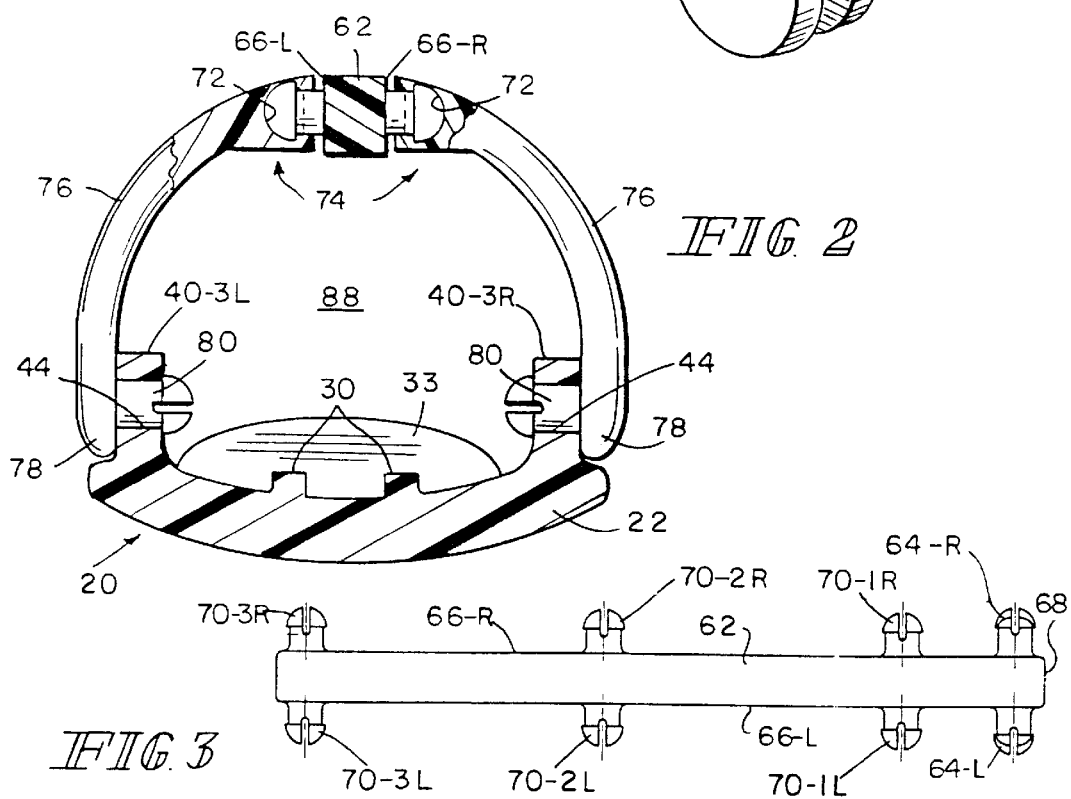
FIG. 2
FIG. 3

SPECULUM

CROSS-REFERENCES TO RELATED APPLICATIONS

This application is a U.S. national application of international application Ser. No. PCT/US99/14838 filed Jun. 30, 1999, which claims priority to U.S. provisional application serial No. 60/092,301 filed Jul. 10, 1998.

FIELD OF THE INVENTION

This invention relates to specula. It is disclosed in the context of a gynecological speculum, but is believed to be useful in other applications as well.

BACKGROUND OF THE INVENTION

Several types of gynecological specula are known. The earlier types are designed and manufactured to be sterilizable. Many of the more recent types are resin or filled resin types, designed and manufactured to be disposable. Many of these later types are molded transparent or semitransparent plastic to assist in examination. Some employ optical waveguiding materials either integrally or as attachments, again to assist in examination. An illustrative, but by no means exhaustive listing of the various known types of specula includes the following U.S. Pat. Nos.: 672,239; 1,150,749; 3,702,606; 3,890,961; 3,985,125; 4,206,750; 4,766,887; 4,884,559; 4,971,036; 5,052,372; 5,072,720; 5,179,937; 5,179,938; 5,458,595; and, 5,499,964. No representation is intended by this listing that the listed references constitute the only, or the closest, relevant art, or that no better references exist. Nor should any such representation be inferred.

DISCLOSURE OF THE INVENTION

A speculum includes at first member, a second member, a third member, and a plurality of fourth members. Each of the fourth members is movably coupled to the first member and to the second member to movably couple the first member to the second member. The third member is movably coupled to the first member and to the second member to actuate the first member and the second member relative to each other between a first orientation in which the speculum is configured to be inserted into an incision, meatus or the like, and a second orientation in which the speculum is configured to aid in examination, treatment or the like, of the incision, meatus or the like.

Illustratively according to the invention, the fourth members are provided in pairs.

Further illustratively according to the invention, each of the fourth members is pivotally coupled to the first member and to the second member.

Additionally illustratively according to the invention, the third member is pivotally coupled to the first member and to the second member.

BRIEF DESCRIPTION OF THE DRAWINGS

The invention may best be understood by referring to the following detailed description and accompanying drawings which illustrate the invention. In the drawings:

FIG. 1 illustrates a perspective view of a speculum constructed according to the invention in a use orientation;

FIG. 2 illustrates a sectional view of the speculum illustrated in FIG. 1, taken generally along section lines 2—2 of FIG. 1;

FIG. 3 illustrates a top plan view of a detail of the speculum illustrated in FIGS. 1–2;

DETAILED DESCRIPTION OF AN ILLUSTRATIVE EMBODIMENT

Figure 4:
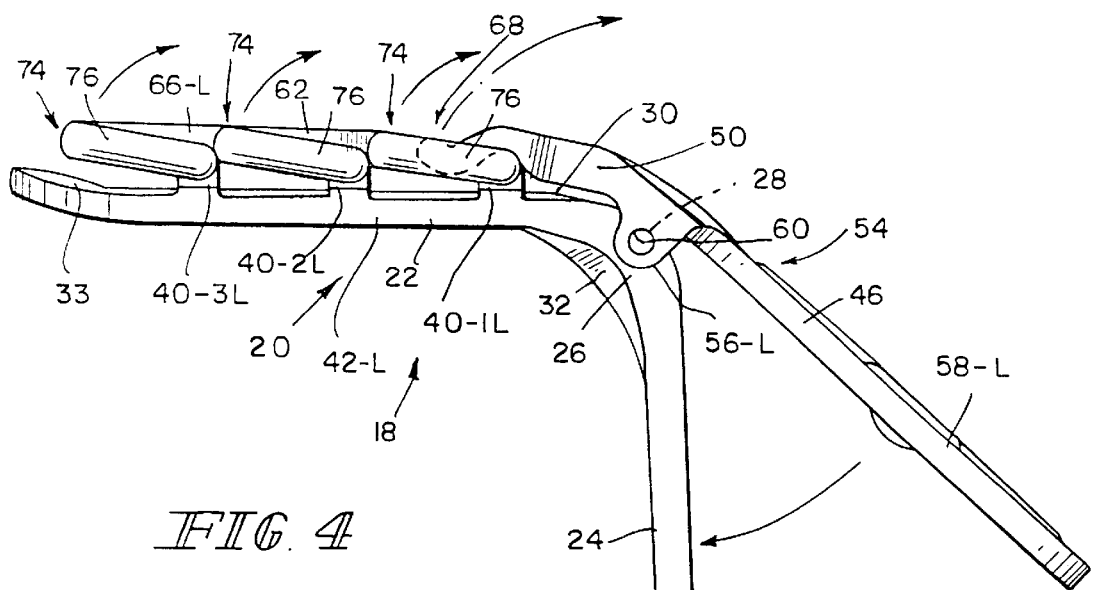
FIG. 4 illustrates a side elevational view of the speculum of FIG. 1 in an insertion orientation, and, FIG. 5 illustrates a side elevational view of the speculum of FIG. 1 in a use orientation.

The speculum of the invention may be constructed from any suitable material or combination of materials, such as filled and/or unfilled resin materials, illustratively to permit its components to be conveniently formed by, for example, injection molding and assembled by, for example, snapping them together. Additionally, if the materials are transparent or semitransparent, this can aid in examination conducted using the speculum. Additionally, if optical waveguiding materials and principles are employed in the design and construction of a speculum constructed according to the invention, this can further aid in examination conducted using the speculum.

Referring now to FIGS. 1–5, the speculum 18 includes a combined first speculum blade and handle portion 20. Portion 20 includes a region 22 generally defining a first speculum blade and a region 24 generally defining a first speculum handle portion. Regions 22, 24 are substantially smoothly integrated in region 26 into a single molded speculum portion 20. A transversely extending, through passageway 28 is formed on portion 20 in region 26. Ribs 30 and webs 32 are molded into portion 20 and extend between regions 22 and 24 through region 26 to strengthen portion 20. The forwardmost end 33 of blade region 22 illustratively includes a generally part circular curvature, perhaps best illustrated in FIG. 1, and a forwardly and upwardly concave curvature, perhaps best illustrated in FIGS. 4–5. Blade region 22 is also provided with a plurality, illustratively three, of pairs of ears 40-1L, 40-1R; 40-2L, 40-2R, and, 40-3L, 40-3R, one of each pair of which extend upwardly from respective opposite lateral edges 42-L and 42-R of blade region 22. Each ear 40-1L, 40-1R, 40-2L, 40-2R, 40-3L and 40-3R is provided with a transversely extending, through passageway 44, best illustrated in FIG. 2.

A speculum handle portion 46 includes at its upper end 48 a pair of upwardly extending drive arms 50, each having a transversely extending, through passageway 52. Downwardly from drive arms 50, toward a central region 54 of handle portion 46, a pair of pivotal mounting ears 56-L and 56-R extend forwardly from respective opposite lateral edges 58-L and 58-R of handle portion 46. Each mounting ear 56-L, 56-R is provided with a transversely extending, through passageway 60. Speculum handle portion 46 is pivotally mounted to portion 20 by one or more pivot pins inserted through aligned passageways 28, 60.

A combined second speculum blade and link portion 62 includes a pair of pivot pins 64-L and 64-R extending from its respective left and right lateral edges 66-L and 66-R adjacent a proximal end 68 of portion 62. Pivot pins 64-L and 64-R are received in respective passageways 52 of respective drive arms 50 to mount portion 62 pivotally from portion 46. Additionally, a plurality, illustratively three, of pairs of pivot pins, 70-1L, 70-1R; 70-2L, 70-2R; 70-3L; 70-3R, best illustrated in FIG. 3, extend from its respective left and right lateral edges 66-L, 66-R. Pivot pins 70-1L, 70-1R, 70-2L, 70-2R, 70-3L, 70-3R are pivotally received in pivotal mounting holes 72, best illustrated in FIG. 2, in first ends 74 of respective combined ribs and links 76. The second ends 78 of combined ribs and links 76 include pivot pins 80, best illustrated in FIG. 2, which are pivotally received in respective through passageways 44 on ears 40-1L, 40-1R, 40-2L, 40-2R, 40-3L and 40-3R of combined first speculum blade and handle portion 20 in the assembled speculum.

Figure 5:
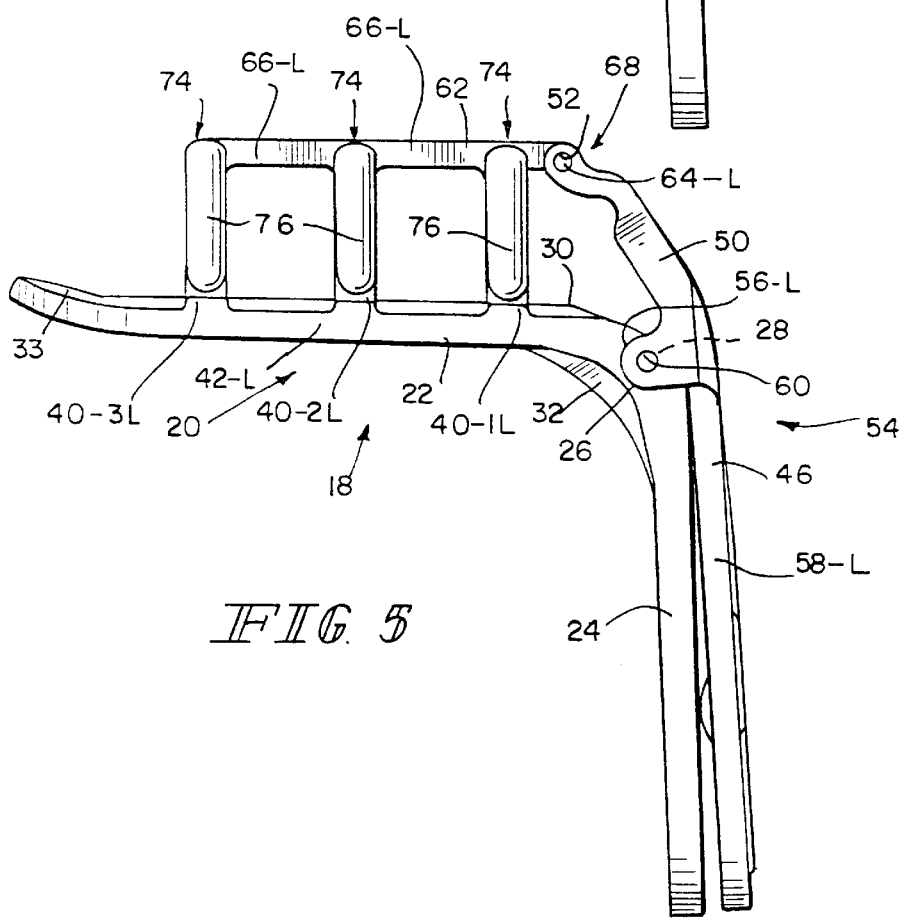

This arrangement mounts second speculum blade and link portion 62 to combined first speculum blade and handle portion 20 so that second speculum blade and link portion 62 can be selectively movably spaced from combined first speculum blade and handle portion 20, as best illustrated by comparing FIGS. 4 and 5, by varying the squeezing pressure between handle portion 46 and region 24 of combined first speculum blade and handle portion 20. In this way, the speculum 18 can be conveniently inserted into a meatus or incision with second speculum blade and link portion 62 collapsed into minimum spacing, illustrated in FIG. 4, from combined first speculum blade and handle portion 20. Then, once the speculum 18 is in position in the meatus or incision, squeezing pressure can be exerted between handle portion 46 and region 24 of combined first speculum blade and handle portion 20 to increase the spacing between second speculum blade and link portion 62 and combined first speculum blade and handle portion 20 to open the meatus or incision for observation and treatment. At the fully open position, with handle portion 46 and region 24 engaged, the speculum 18 can be so designed that the second speculum blade and link portion 62 is in an over-center orientation with respect to combined first speculum blade and handle portion 20, locking portions 20 and 62 in this orientation. This can best be appreciated with reference to FIGS. 1 and 5. Opening of the spacing between second speculum blade and link portion 62 and combined first speculum blade, and handle portion 20 also provides a pathway 88 through the speculum 18 for the insertion into the meatus or incision of instruments for treatment. The space 90, best illustrated in FIG. 1, between drive arms 50 also promotes such insertion.

What is claimed is:

1. A speculum including a first member having a first blade portion and a first handle portion, said first blade portion having a forwardmost end exhibiting a forwardly and upwardly concave curvature, a second member having a second blade portion, a third member having a second handle portion, and a plurality of fourth members, each of the fourth members being movably coupled to the first blade portion and to the second blade portion to movably couple the first blade portion to the second blade portion, the third member being movably coupled to the first member and to the second member actuate the first blade portion and the second blade portion relative to each other between a first orientation wherein the first blade portion and the second blade portion are adjacent one another and a second orientation wherein the first blade portion and the second blade portion are spaced a distance apart from one another and the first handle portion of the first member and the second handle portion of the third member cooperate in the second orientation to limit the distance that the first blade portion and the second blade portion may be spaced apart.

2. The apparatus of claim 1 wherein each of the first and second members includes opposite first and second sides, and the fourth members are provided in pairs, one fourth member of each pair extending between a respective first or second side of the first member and a respective first or second side of the second member.

3. The apparatus of claim 2 wherein each of the fourth members is pivotally coupled to the first member and to the second member.

4. The apparatus of claim 3 wherein the third member is pivotally coupled to the first member and to the second member.

5. The apparatus of claim 2 wherein the third member is pivotally coupled to the first member and to the second member.

6. The apparatus of claim 1 wherein each of the fourth members is pivotally coupled to the first member and to the second member.

7. The apparatus of claim 6 wherein the third member is pivotally coupled to the first member and to the second member.

8. The apparatus of claim 6 wherein the fourth members are provided in pairs.

9. The apparatus of claim 1 wherein the third member is pivotally coupled to the first member and to the second member.

10. The apparatus of claim 9 wherein the fourth members are provided in pairs, each of the fourth members being pivotally coupled to the first member and to the second member.

11. The apparatus of claim 1 wherein the fourth members are provided in pairs, each of the fourth members being pivotally coupled to the first member and to the second member.

12. A spectrum including a first member having a first blade portion and a first handle portion, a second member, having a second blade portion, a third member having a second handle portion, and a plurality of fourth members, each of the fourth members being movably coupled to the first blade portion and to the second blade portion to movably couple the first blade portion to the second blade portion, the third member being movably coupled to the first member and to the second member to to actuate the first blade portion and the second blade portion relative to each other between a first orientation wherein the first blade portion and second blade portion are adjacent one another and a second orientation wherein the first blade portion and second blade portion are spaced a distance apart from one another and the first handle portion of the first member and the second handle portion of the third member cooperate in the second orientation to limit the distance that the first blade portion and second blade portion may be spaced apart.

13. The apparatus of claim 12 wherein each of the first and second members includes opposite first and second sides, and the fourth members are provided in pairs, one fourth member of each pair extending between a respective first or second side of the first member and a respective first or second side of the second member.

14. The apparatus of claim 13 wherein each of the fourth members is pivotally coupled to the first member and to the second member.

15. The apparatus of claim 14 wherein the third member is pivotally coupled the first member and to the second member.

16. The apparatus of claim 15 wherein the plurality of the fourth members cooperate with the first and third members to block movement of the first member and second member relative to each other when the first and second members are in the second orientation.

* * * * *

UNITED STATES PATENT AND TRADEMARK OFFICE
CERTIFICATE OF CORRECTION

PATENT NO. : 6,527,710 B1
DATED : March 4, 2003
INVENTOR(S) : Davidson et al.

It is certified that error appears in the above-identified patent and that said Letters Patent is hereby corrected as shown below:

<u>Column 3,</u>
Line 49, insert -- to -- after "member".

Signed and Sealed this

Ninth Day of December, 2003

JAMES E. ROGAN
*Director of the United States Patent and Trademark Office*